United States Patent [19]
Terstappen et al.

[11] Patent Number: 5,840,580
[45] Date of Patent: Nov. 24, 1998

[54] PHENOTYPIC CHARACTERIZATION OF THE HEMATOPOIETIC STEM CELL

[75] Inventors: Leon W. Terstappen, Huntingdon Valley, Pa.; Michael R. Loken, Mercer Island, Wash.; Shiang Huang, San Ramon, Calif.; Johanna Olweus; Fridtjof Lund-Johansen, both of Fremont, Calif.

[73] Assignee: Becton Dickinson and Company, Franklin Lakes, N.J.

[21] Appl. No.: 856,406

[22] Filed: May 14, 1997

Related U.S. Application Data

[63] Continuation of Ser. No. 358,038, Dec. 15, 1994, abandoned, which is a continuation of Ser. No. 169,912, Dec. 20, 1993, abandoned, which is a continuation-in-part of Ser. No. 895,491, Jun. 8, 1992, abandoned, which is a continuation-in-part of Ser. No. 759,092, Sep. 6, 1991, abandoned, which is a continuation of Ser. No. 517,101, May 1, 1990, abandoned.

[51] Int. Cl.$^6$ .............................. A01N 63/00; C12N 5/06; C12N 5/08
[52] U.S. Cl. .......................... 435/372; 424/93.1; 435/325; 435/326
[58] Field of Search ........................... 424/93.1; 435/325, 435/326, 372

[56] References Cited

U.S. PATENT DOCUMENTS 5,061,620  10/1991  Tsukamoto et al. .................... 435/7.21

FOREIGN PATENT DOCUMENTS 0 455 482 A2  5/1991  European Pat. Off. .
WO 93/25216  6/1992  WIPO .

OTHER PUBLICATIONS

L. Terstappen, et al, "Formation of Hematopoietic Microenvironment and Hematopoietic Stem Cells from single Human Bone Marrow Stem Cells" Nature, 360, pp. 745–749 (Dec. 1992).

L. Terstappen, et al, "Lymphoid and Myeloid Differentiation of Single Human CD34+, HLA–DR+, CD– Hematopoietic Stem Cells" Blood, 83(6), pp. 1515–1526 (Mar. 15, 1994).

L. Terstappen, et al, "Characterization of CD34+, CD38–, HLA–DR–Common Stem Cells" Annual Meeting, ASH, Abst. 705 (Nov. 1993).

L. Terstappen, et al, "Characterization of CD34+/CD38– Acute Myeloid Leukemia", Annual Meeting, ASH, Abst. 471 (Nov. 1993).

L. Terstappen, et al, "Selective Outgrowth of Human Primitive CD34+, CD38–, HLA–DR+ Hematopoietic Progenitor Cells", Annual Meeting, ASH, Abst. 50 (Nov. 1993).

Science 270: 1751,1995 (Marshave).

Science 269: 1050, 1995 (Marshave).

Donahue et al JEM 176: 1125, 1992.

Coghlan et al New Scientist, p. 14, 1995 Report and Recommendations of the Panel to assess the NIH investment in Research on Gene Therapy, Dec. 7, 1995.

Appendix A, Fourth International Workshop on Human Leucocyte Differentiation Antigens, Oxford Univ. Press 1989.

Friedman Science 244: 1275, 1989.

Siena et al Blood 74(6): 1905, 1989.

Williams Human Gene Therapy 1: 229, 1990.

Terstappen et al Leucocyte Biology 48: 138, 1990.

*Primary Examiner*—Brian R. Stanton
*Attorney, Agent, or Firm*—Royal N. Ronning, Jr.; Susan A. Capello

[57] ABSTRACT

One or more population of cells enriched for human hematopoietic stem cells is disclosed. HSC in this population of cells are capable of limited self-renewal and are capable of differentiating into all elements of the hematopoietic system. This population of cells has the phenotype of $CD34^+/CD38^-$ and more preferably $CD34^+/CD38^-/HLA\text{-}DR^+$. Cells within this population have been found to express CD13, CD33 and CD71. Hematopoietic stem cells can be used in a number of therapies, including autologous transplantation and in gene therapy.

9 Claims, 13 Drawing Sheets
(12 of 13 Drawing Sheet(s) Filed in Color)

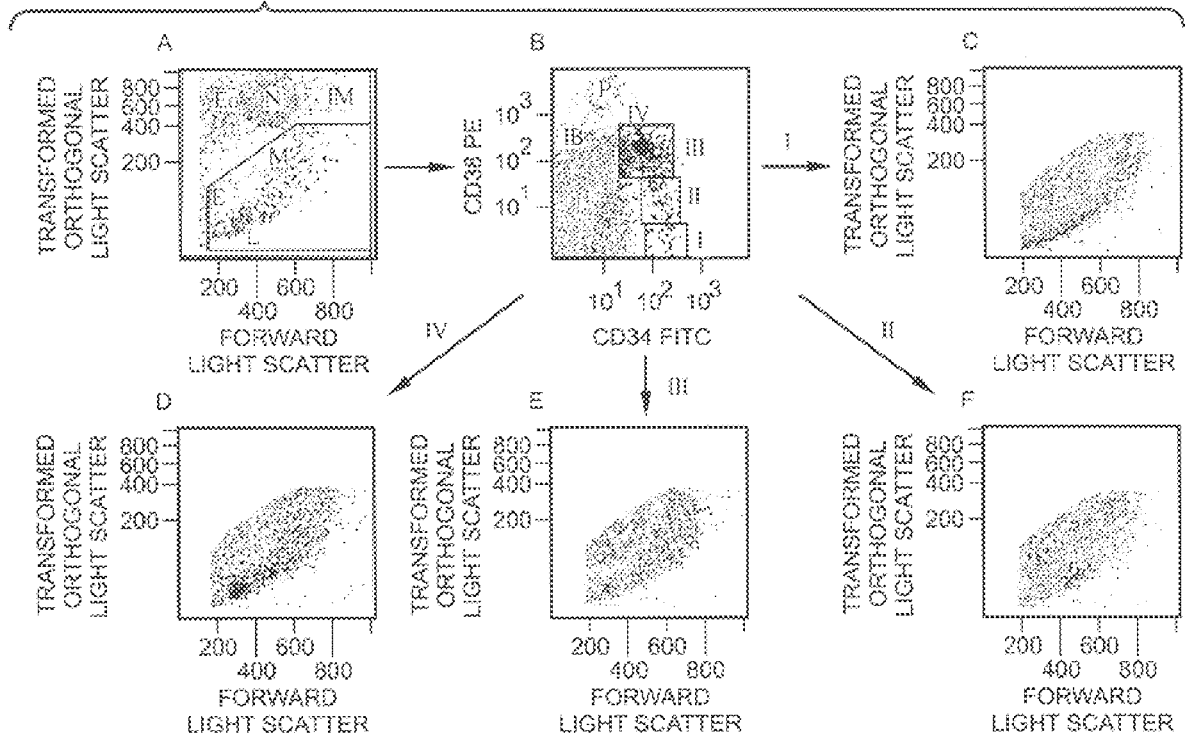

PHENOTYPIC CHARACTERIZATION OF THE HEMATOPOIETIC STEM CELL

This application is a continuation of application Ser. No. 08/358,038, filed Dec. 15, 1994, now abandoned, which is a continuation of application Ser. No. 08/169,912, filed Dec. 20, 1993, now abandoned, which is a continuation-in-part of U.S. Ser. No. 07/895,491, filed 8 Jun. 1992 now abandoned, which is a continuation-in-part of U.S. Ser. No. 07/759,092, filed 6 Sep. 1991 now abandoned, which is a continuation of U.S. Ser. No. 07/517,101, filed 1 May 1990, now abandoned.

FIELD OF THE INVENTION

This invention relates to one or more populations of human cells that are enriched for hematopoietic stem cells ("HSC"). The invention more particularly relates to methods to identify and purify cell populations enriched for HSC, and further relates to the use of HSC enriched cells in one or more therapies.

BACKGROUND OF THE INVENTION

The human hematopoietic system comprises nucleated and non-nucleated cells of several different types that reside principally in the peripheral blood and bone marrow. For example, there are T and B lymphocytes, monocytes, granulocytes, megakaryocytes and erythrocytes. Each of these cell types traditionally has been distinguished based on well known morphological features (which may be observed using traditional staining methods combine with light microscopy), and more recently, by expression of certain cell surface antigens. For example, Loken et al., Blood, 70:1316 (1987), used flow cytometry and a combination of light scatter and immunofluorescence staining to identify the various stages of B lymphocyte maturation.

Working backward from the most mature cell to the most immature cell within a cell type, Loken et al. showed that certain antigens are expressed on mature stages of cells but not on immature stages and vice versa. Loken et al. also showed that cells of different types showed greater similarities in the expression of antigens found at immaturity. Thus, for example, neutrophils, eosinophils and basophils at maturity express certain different antigens and have different cell functions yet all arise from myeloid progenitors. Red blood cells arise from erythroid progenitors. The same is believed to be true for lymphocytes with NK cells, T and B lymphocytes arise from lymphoid progenitors. These progenitor cells, however, were not believed to be the earliest hematopoietic cell type. It had long been speculated that there were hematopoietic stem cells that gave rise to all progenitor cells which then differentiated into each of the various lineages of cells. Accordingly, HSC are defined as those cells that are capable of both limited self-renewal and differentiation into the three principle progenitor components (i.e., erythroid, lymphoid and myeloid. In this application, megakaryocytes are considered part of the myeloid lineage, and NK cells are considered part of the lymphoid lineage.)

Although a number of scientists have been exploring multiple means for isolating stem cells, the first breakthrough into stem cell isolation and identification did not come until the early 1980's. In U.S. Pat. No. 4,714,680, Civin described a population of "pluripotent lympho-hematopoietic cells which were substantially free of mature lymphoid and myeloid cells." Civin also described an antigen, MY-10 and a monoclonal antibody (of the same name) thereto, which was present on these pluripotent cells. These "pluripotent lympho-hematopoietic" cells make up to about 1% of all cells in normal adult bone marrow, and generally comprise a mixture of HSC and lineage committed progenitor cells with the latter cells predominating.

Since that time, MY-10 has been classified by the International Workshop on Human Leukocyte Antigens as falling with the cluster designated as "CD34." CD34 monoclonal antibodies are commercially available from a number of sources including Becton Dickinson Immunocytometry Systems, San Jose, Calif. ("BDIS").

CD34 monoclonal antibodies have been used for a number of purposes. As noted above, Loken, Terstappen and their collaborators published a series of papers describing the maturational stages for various components of the hematopoietic system (e.g., T and B lymphocytes, erythroid cells and neutrophils). The purpose of this work was to define, starting from the most mature cell and working backwards, the phenotype of various maturational and developmental stages that lineage committed cells go through.

While the focus of this body of work has been on maturational stages within lineage committed cells, others have used CD34 monoclonal antibodies to look for earlier non-lineage committed stem cells. In Terstappen et al., Blood, 77:1218 (1991), the authors described a subset of human cells some of which were capable of limited self-renewal and differentiation into each of the various hematopoietic lineages. This population was characterized, phenotypically, as being "$CD34^+/CD38^-$." These cells were shown by conventional flow cytometry not to express a number of antigens commonly believed to be indicative of "lineage commitment" (i.e., CD33, CD71, CD5 and CD10).

Others, including Andrews et al., J. Exp. Med., 355 (1990), Andrews et al., J. Exp. Med., 1721 (1989), and Berenson et al., J. Clin. Invest., 81:951 (1988), used CD34 monoclonal antibodies in combination with one or more lineage associated antibodies to subset $CD34^+$ cells. Again, focusing on the fact that certain antigens were assumed to be indicative of lineage commitment or maturation, these researchers attempted to look for positive expression of CD34 and negative expression of these other antigens. They then isolated and characterized a number of different $CD34^+$ subsets. The cells within these subsets (e.g., $CD34^+/CD33^-$) were thought to be more immature and be enriched for HSC.

Sutherland et al., Blood, 74:1563 (1989), used CD34 and HLA-DR antibodies to subset $CD34^+$ cells. They examined three different cell populations for the presence of long term initiating cells. The three populations were $CD34^+/HLA-DR^-$, $CD34^+/HLA-DR^{low}$ and $CD34^+/HLA-DR^+$. They found that the $CD34^+/HLA-DR^{low}$ cells were enriched for long term initiating cells that are believed to contain HSC.

Verfaille et al., J. Exp. Med., 172:509 (1990), reported on an $CD34^+/HLA-DR^+$ and $CD34^+/HLA-DR^-$ population of "primitive" progenitor cells. Taking adult marrow, Verfaille et al. depleted bone marrow of "$Lineage^+$" cells using multiple monoclonal antibodies. In a second step, fluorescently labelled CD34 and HLA-DR monoclonal antibodies were used to select $HLA-DR^+$ and $HLA-DR^-$ populations that also were $CD34^+$. Having isolated these two groups, Verfaille et al. reported that the $HLA-DR^+$ cells were better in short term culture than $HLA-DR^-$ cells. In long term culture, the reverse was true.

Tsukamoto et al. described a population of cells which also were capable of self-renewal and differentiation; however, this population of cells was characterized, phenotypically, as "$CD34^+/CD10^-/CD19^-/CD33^-$ and Thy- 1+." These so called CD34+/"Lineage−" cells are described in U.S. Pat. No. 5,061,620.

In each of the references described above, conventional flow cytometry was used, and researchers consistently identified populations of cells believed to be enriched for HSC as being CD34+ and lacking expression of antigens commonly associated with lineage commitment (i.e., CD13/CD33 [myeloid] and CD71 [erythroid]). In fact, as noted above, most researchers have used a depletion strategy (i.e., to use antibodies to lineage associated antigens, such as CD33) in order to purify their cell preparations before positive selection with CD34.

In order to test completely this approach, a high-resolution, multi-parameter flow cytometer has been designed in order to look more carefully at antigens possibly expressed at low densities. Surprisingly, it now has been found that these prior approaches may have eliminated some HSC from the cell populations. A population of human cells that is devoid of mature and progenitor erythroid, lymphoid and myeloid cells and that is enriched for HSC now is shown to be not only CD34+/CD38−/HLA-DR+ but also CD13+, CD33+ and CD71+.

SUMMARY OF THE INVENTION

This invention comprises a population of human cells that is enriched for hematopoietic stem cells. HSC within this population of cells are capable of limited self-renewal and are capable of differentiating into each of the hematopoietic progenitor cell lines. HSC are enriched in a population of human cells that lacks mature and progenitor cells of the erythroid, lymphoid and myeloid lineage.

A population of cells having these properties comprise cells that have the phenotype CD34+/CD38−. In this population of cells, HSC comprise at least 10–15% of the cells when the cells are taken from normal adult bone marrow. Higher levels of enrichment for HSC are found in that population of human cells that are also HLA-DR+. In this population of cells, HSC comprise at least 20% of the cells when the cells are taken from normal fetal bone marrow. Surprisingly, a population of human cells that is enriched for HSC also have been found to express certain lineage associated antigens (i.e., CD13, CD33 and CD71) but not others (e.g., CD3, CD5, CD8, CD10, CD11b, CD15, CD16, CD20, CD22 and CD61). Thus, the phenotype of a population of human cells that is highly enriched for HSC comprise cells having the phenotype CD34+/CD38−/HLA-DR+ and CD13+, CD33+ and CD71+.

Populations of human cells that are enriched for HSC can be obtained from adult and fetal peripheral blood, cord blood, bone marrow, liver or spleen. Preferably, these cells are obtained in bone marrow or peripheral blood. They may be obtained after mobilization of the cells in vivo by means of growth factor treatment.

A population of human cells that is enriched for HSC can be identified by using a combination of markers, such as antibodies (or antibody derived reagents, such a single chain binding proteins, and nucleic acid binding fragments, such as described in U.S. Pat. No. 5,270,163) and selecting for the presence or absence of the antigens recognized by those markers on the cells. Preferably, monoclonal antibodies are used, and the combination of antibodies comprises at least two monoclonal antibodies (i.e., CD34 and CD38), and more preferably comprises at least three antibodies (e.g., CD34, CD38 and HLA-DR). Surprisingly, it has been shown that CD38 has a unique ability to mark mature and progenitor cells thereby allowing the negative selection for CD38 to exclude such mature and progenitor cells but not those cells that are non-lineage committed and have multi-lineage potential.

A population of human cells that is enriched for HSC can be isolated using the combination of antibodies described above to identify HSC. Methods for isolation include flow cytometry, wherein HSC are selected for the expression of CD34 but not CD38 and also the expression of HLA-DR, and include multi-step bead or biotin based selection wherein each of the antibodies is conjugated to avidin or a magnetic bead and then the sample containing HSC is passed through a column or other device so that, in the first pass, for example, CD34+ cells are selected, then CD38− cells that are CD34+ are selected, followed by selection for those CD34+/CD38− cells that are HLA-DR+. Strategies that start with the depletion of cells bearing lineage associated antigens, such as CD33, CD13 or CD71, however, these strategies can remove HSC from the desired population of human cells if the method of removal selects for antigens expressed at low densities.

Populations of human cells that are enriched for HSC can be used in a variety of therapies. Among the therapies include the treatment of leukemias, lymphomas and solid tissue tumors, such as breast cancer. In these treatments, populations of human cells that are enriched for HSC can be given to a patient whose marrow has been destroyed by ablative therapy.

Further therapies include the genetic manipulation of HSC and subsequent transplantation into blood or bone marrow. Examples of genes that could be transfected into HSC include genes whose products confer resistance to HIV viral replication, genes related to multi-drug resistance ("MDR"), and adenosine deaminase ("ADA"). The source of human cells for any therapeutic treatment involving HSC may be autologous or allogeneic. Autologous sources are preferred.

BRIEF DESCRIPTION OF THE FIGURES

The file of this patent contains at least one figure executed in color. Copies of this patent color figure(s) will be provided by the Patent and Trademark Office upon request and payment of necessary fee.

FIGS. 1A–F comprise a series of six dot plots of normal adult bone marrow cells that have been labelled with anti-CD34 FITC (fluorescein isothiocyanate) and anti-CD38 PE (r-phycoerythrin) and then analyzed by means of standard flow cytometry wherein 1A is a plot of transformed orthogonal light scatter versus forward light scatter, 1B is a plot of log PE versus log FITC fluorescence for the cells within the gate drawn in 1A, 1C is a plot of transformed orthogonal light scatter versus forward light scatter for the cells within the gate marked "I" in 1B, 1D is a plot of transformed orthogonal light scatter versus forward light scatter for the cells marked "IV" in 1B, 1E is a plot of transformed orthogonal light scatter versus forward light scatter for the cells within the gate marked "III" in 1B, and 1F is a plot of transformed orthogonal light scatter versus forward light scatter for the cells within the gate marked "II" in 1B;

Figure 2A:
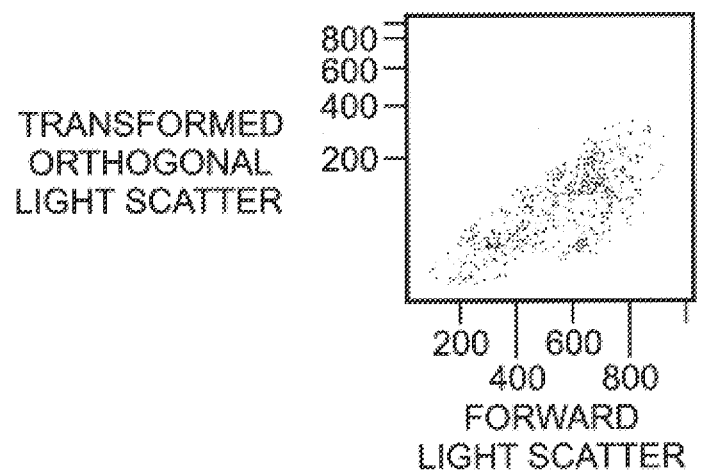
FIGS. 2A–B comprise four dot plots of fetal bone marrow cells that have been labelled with anti-CD34 FITC, anti-CD38 PE and anti-HLA-DR APC (allophycocyanin) wherein 2A is a plot of transformed orthogonal light scatter versus forward light scatter, 2B is a plot of log PE versus log FITC fluorescence, 2C is a plot of log APC versus log FITC fluorescence, and 2D is a plot of log PE versus log APC fluorescence and further wherein CD34+/CD38−/HLA-DR− cells are colored red, CD34+/CD38−/HLA-DR+ cells are colored yellow, CD34+/CD38+/HLA-DR− cells are colored blue, and CD34+/CD38+/HLA-DR+ cells are colored gray.
Figure 2B:
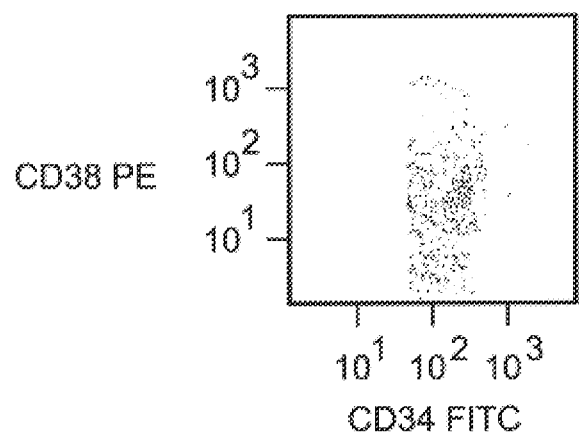
Figure 2C:
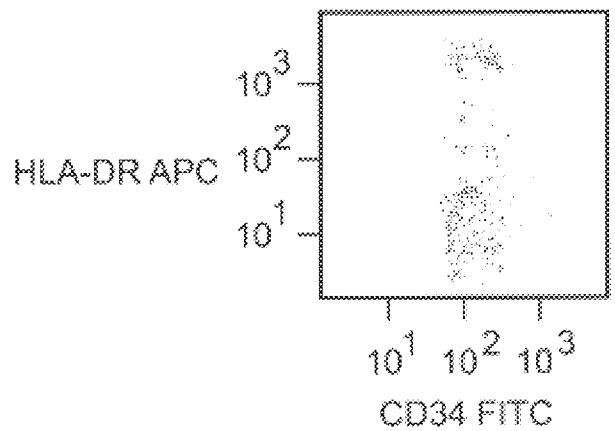
Figure 2D:
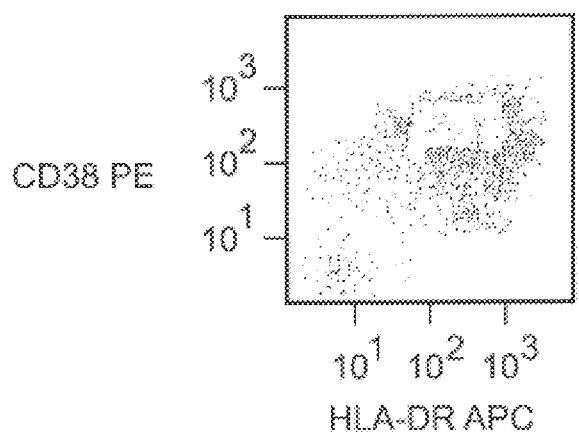
Figure 3A:
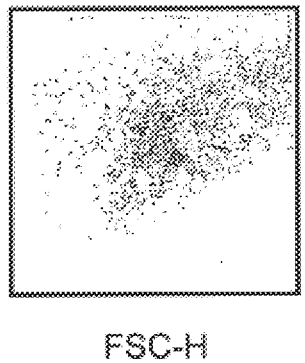
Figure 3B:
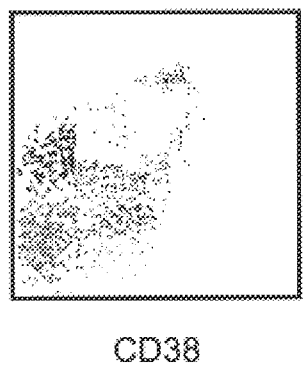
Figure 3C:
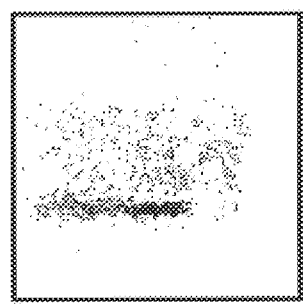
Figure 3D:
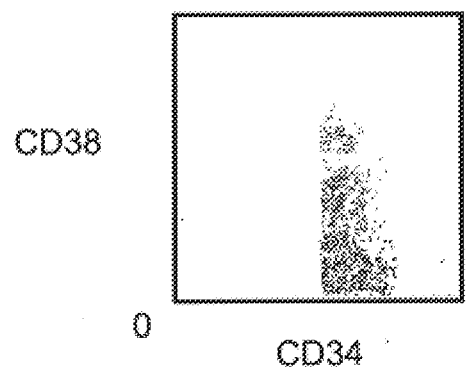
Figure 3E:
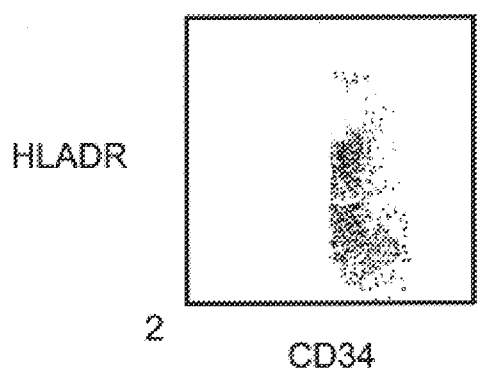
Figure 3F:
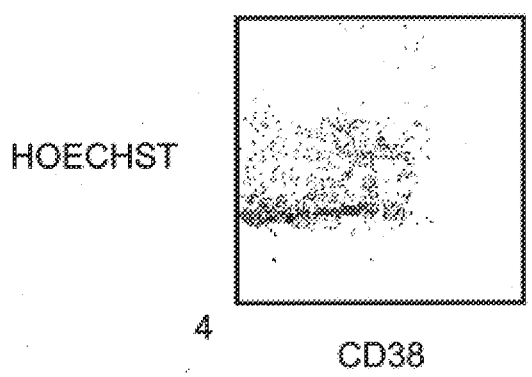

FIGS. 3A–F comprise a series of six dot plots of fetal bone marrow cells that have been labelled with Hoechst 33343, anti-CD34 FITC, anti-CD38 PE and anti-HLA-DR PE-CY5 wherein 3A is a plot of transformed orthogonal light scatter versus forward light scatter, 3B is a plot of log PE versus log PE-CY5 fluorescence, 3C is a plot of Hoechst 33343 versus log PE-CY5 fluorescence, 3D is a plot of log FITC versus log PE fluorescence, 3E is a plot of log FITC versus log PE-CY5 fluorescence, and 3F is a plot of Hoechst 33343 versus log PE fluorescence, however, only those cells that are CD34+ are displayed in each plot.

FIGS. 4A–E comprise a series of five dot plots of fetal bone marrow cells that have been labelled with anti-CD34 PerCP, anti-CD38 APC and anti-HLA-DR FITC wherein 4A is a plot of log PerCP fluorescence versus transformed orthogonal light scatter, 4B is a plot of log APC versus log PerCP fluorescence, 4C is a plot of log FITC versus transformed orthogonal light scatter, 4D is a plot of log APC versus transformed orthogonal light scatter, and 4E is a plot of log APC versus log FITC fluorescence.

FIGS. 5A–F comprise a series of six dot plots of fetal bone marrow cells that have been labelled with anti-CD34 PerCP, anti-CD38 APC, anti-CD13 PE and anti-HLA-DR FITC wherein 5A is a plot of log PE fluorescence versus transformed orthogonal light scatter, 5B is a plot of log PE versus log PerCP fluorescence, 5C is a plot of transformed orthogonal light scatter versus forward light scatter, 5D is a plot of log PE versus forward light scatter, 5E is a plot of log PE versus log FITC fluorescence, and 5F is a plot of log PE versus log APC fluorescence wherein CD34+/CD38−/HLA-DR+ cells are colored green, CD34+/CD38−/HLA-DR− cells are colored red, myeloid committed cells are colored gray and lymphoid committed cells are colored yellow.

FIGS. 6A–F comprise a series of six dot plots of fetal bone marrow cells that have been labelled with anti-CD34 PerCP, anti-CD38 APC, anti-CD33 PE and anti-HLA-DR FITC wherein 6A is a plot of log PE fluorescence versus transformed orthogonal light scatter, 6B is a plot of log PE versus log PerCP fluorescence, 6C is a plot of transformed orthogonal light scatter versus forward light scatter, 6D is a plot a log PE versus forward light scatter, 6E is a plot of log PE versus log FITC fluorescence, and 6F is a plot of log PE versus log APC fluorescence wherein CD34+/CD38−/HLA-DR+ cells are colored green, CD34+/CD38−/HLA-DR− cells are colored red, myeloid committed cells are colored gray and lymphoid committed cells are colored yellow.

FIGS. 7A–F comprise a series of six dot plots of fetal bone marrow cells that have been labelled with anti-CD34 PerCP, anti-CD38 APC, anti-CD71 PE and anti-HLA-DR FITC wherein 7A is a plot of log PE fluorescence versus transformed orthogonal light scatter, 7B is a plot of log PE versus log PerCP fluorescence, 7C is a plot of transformed orthogonal light scatter versus forward light scatter, 7D is a plot a log PE versus forward light scatter, 7E is a plot of log PE versus log FITC fluorescence, and 7F is a plot of log PE versus log APC fluorescence wherein CD34+/CD38−/HLA-DR+ cells are colored green, CD34+/CD38−/HLA-DR− cells are colored red, myeloid committed cells are colored gray and lymphoid committed cells are colored yellow.

DETAILED DESCRIPTION

For FIG. 1, bone marrow aspirates were obtained from consenting normal adult volunteers. Erythrocytes were lysed using $NH_4Cl$. The cells then were stained with anti-CD38 PE and anti-CD34 (FITC) (commercially available from BDIS as Leu-17 PE and HPCA-1 FITC). Cells were analyzed on a standard FACScan flow cytometer (BDIS). Data acquisition was performed with FACScan Research software (BDIS). Forward light scatter, orthogonal light scatter and two fluorescence signals were determined for each cell and stored in listmode files. Each experiment measured approximately 30,000 events. The analysis of the listmode data files was performed with PAINT-A-GATE software (BDIS). (See also U.S. Pat. No. 4,845,653.) Orthogonal light scatter data was transformed by the method disclosed in U.S. Pat. No. 5,224,058.

Referring to FIG. 1A, this figure shows the correlative display of forward and transformed orthogonal light scatter. CD34+ cells appear black whereas all other cells are depicted gray. The position of the major cell types are indicated with "Eo" for eosinophils, "N" for neutrophils, "IM" for immature myeloid cells, "M" for monocytes, "L" for lymphocytes and "E" for mature nucleated erythroid cells. A gate was applied on a light scattering region in which the black colored cells appeared. Using this light scattering gate, an additional 30,000 events were scanned in listmode, and the correlative display is shown in FIG. 1B.

As in FIG. 1A, the CD34+ cells in FIG. 1B are depicted black and all other cells are depicted gray. The position of the previously described CD38 bright plasma cells and immature b lymphocytes are indicated with "P" and "IB" respectively. Four populations of CD34+ cells were distinguished based upon differential expression of the CD34 and CD38 antigens. Stage P I is the smallest population (in terms of numbers of cells), and brightly expresses CD34 but does not express CD38. Stage P I appears in a specific light scattering region as is illustrated in FIG. 1C. The morphology of these P I cells, as determined by Wright-Giemsa staining and light microscopy, showed a strikingly homogeneous population of cells slightly larger than lymphocytes. The cells in this population lack (i.e., by morphology contain less than 5%) mature and progenitor cells of the erythroid, lymphoid and myeloid lineages.

Stage P II cells were characterized by a low density expression of CD38 and a slight decrease in the expression of CD34. The P II cells appeared in a light scattering region similar to P I cells. See FIG. 1F. The morphology of the P II cells is comparable to those of P I; however, there appears to be more heterogeneity. This population too lacks mature erythroid, lymphoid and myeloid cells.

Stage P III cells were characterized by a large density of CD38 and an intermediate density of CD34 expression. With respect to light scattering, this population was heterogeneous with a population of relatively low light scattering signals and a population of relatively large light scattering signals. See FIG. 1E. This heterogeneity was confirmed by morphological examination. Blast cells of the erythroid, lymphoid and myeloid lineages were observed in this cell fraction.

Stage P IV cells were characterized by a large density of the CD38 antigen and dim expression of the CD34 antigen. The light scattering properties of this population was even more dispersed as compared with the P III cells. See FIG. 1D. The morphology of the cells revealed blasts of multiple cell lineages differentiated slightly more than those compared with P III cells.

In 10 normal bone marrow aspirates, the frequency of P I cells in the sample was less than 0.01% of all cells. The frequency of P I cells was approximately 1% of all CD34+ cells.

Cells from each of the four stages were sorted into individual wells and their ability to form blast colonies was determined. Single cells from each of the four stages were plated in 72 well plates containing liquid media for single cell culture. Each well contained a mixture 20 μl mixture of IMDM, 2% fetal calf serum ("FCS"), 1% bovine serum albumin ("BSA"), $5 \times 10^{-5}$M 2-mercaptoethanol, 600 μg/ml transferrin, 10 μg/ml soybean lecithin and antibiotics. No growth factors were added until day 14 of incubation. This was done so as to further enrich for quiescent HSC by permitting all those cells that were growing (i.e., progenitor cells) to die off. See, Leary et al., Blood, 69:593 (1987). rhIL-3, IL-6, granulocyte/monocyte-colony stimulating factor ("GM-CSF"), and erythropoietin ("EPO") then were added to each well at a final concentration of 100 U/ml with the exception of EPO which was added at 2.5 U/ml. All cultures were incubated in 5% $CO_2$ in air at 37° C. in a fully humidified incubator. The plates were observed between days 24 and 34 for the appearance of blast colonies. Replating efficiency was determined by scoring colonies on days 7–14 after replating of the individual dispersed blast colonies in 96-well flat bottom plates containing the growth factor supplement medium used above. The results are set forth in Table I.

TABLE I

Plating Efficiency of Single Cells in the Four Identified States for Colony Formation as a Percentage

| Exp | Day | Stage I | Stage II | Stage III | Stage IV | Day |
|---|---|---|---|---|---|---|
| 1 | 28–34 | 30.3 | 7.0 | 5.6 | 0.0 | 40–47 |
| 2 | 28–34 | 25.1 | 2.8 | 0.0 | 1.4 | 40–47 |
| 3 | 28–34 | 25.3 | 1.8 | 2.8 | 2.4 | 40–47 |
| 4 | 28–34 | 18.8 | 8.5 | 2.1 | 0.0 | 40–47 |

As can be seen, cells in Stage P I form the greater percentage of blast colonies when compared with later stages. The replating efficiency of blast colonies was significant. This indicates that the $CD34^+/CD38^-$ cells contain a high percentage of blast colony forming cells. Thus, at least 15–20% of the cells, as defined by this assay, comprise HSC.

In another experiment, the ability to continually replate cells was examined over a course of 5 generations. In Table II, Stage P I cells were replated from single well blast colonies. As can be seen, the cells from Stage P I have the ability to form blasts through at least 5 generations of replating. Accordingly, cells included within this stage have limited self-renewal capacity which is a function and characteristic of a HSC.

TABLE II

Multi-Generation Colony Formation of CFU-Blast

| Exp | Gen 1 | Gen 2 | Gen 3 | Gen 4 | Gen 5 | Gen 6 |
|---|---|---|---|---|---|---|
| 1 | 1 | $3^a/3^b$ | 7/4 | 61/20 | 9/9 | 1 |
|  | 1 | 1/1 | 5/3 | 17/10 | 3/3 | 0 |
|  | 1 | 2/2 | 4/3 | 13/10 | 2/2 | 0 |
|  | 1 | 1/1 | 4/2 | 15/10 | 2/2 | 0 |
| 2 | 1 | 1/1 | 5/2 | 13/8 | 2/2 | 0 |
|  | 1 | 3/3 | 6/3 | 21/10 | 5/5 | 1 |
|  | 1 | 1/1 | 3/1 | 11/5 | 2/2 | 0 |

[a] number of colonies found
[b] number of colonies replated (only vital appearing colonies were replated)

For FIGS. 2–3, fetal bone marrows were obtained from aborted fetuses 16–22 weeks of gestational age and used following the guidelines of the institutional review board of Stanford University Medical Center on the use of Human Subjects in Medica Research. Fetal bone marrow cells were isolated by flushing intramedullary cavities of the femurs with RPMI 1640 with 10% FCS followed by density dependent centrifugation. The cells were labelled with anti-CD34 FITC (HPCA-2 FITC, BDIS), anti-CD38 PE (Leu 17 PE, BDIS) and anti-HLA-DR biotin followed by an incubation with Streptavidin Allophycocyanin or Streptavidin PE-CY5.

Cell sorting was performed on a standard $FACStar^{Plus}$ cell sorter using the Automated Cell Deposition Unit (BDIS) equipped with an Argon laser tuned to 488 nm and a Helium Neon laser tuned to 633 nm. The cells colored red, yellow, blue and gray in FIG. 2, were sorted singly into 96 well flat bottom plates. In the liquid culture system, each well contained a 200 μl mixture of alpha medium, 12.5% horse serum, 12.5% FCS, $10^{-4}$M 2-mercaptoethanol, 2 nM L-glutamine, 0.2 mM i-inositol, 20 μM folic acid, antibiotics, 2.5 ng/ml beta-fibroblast growth factor ("β-FGF"), 10 ng/ml IGF-1, 10 ng/ml rhIL-3, 500 U/ml rhIL-6, 10 ng/ml GM-CSF (Collaborative Biomedical Products), 2.5 U/ml rhEPO (Amgen) and 50 ng/ml human stem cell factor ("hSCF") (Genzyme) (hereinafter "HSC Growth Medium"). Flow cytometric analyses were performed on the same instrument using Lysis 2.0 data acquisition software (BDIS) with gates set on light scattering and $CD34^+$ cells. Forward light scattering, orthogonal light scattering and three fluorescence signals were determined for each event and approximately 10,000 events were stored in listmode data files. Data analysis and light scatter transformation were performed as described above.

Referring to FIG. 2, in three color immunofluorescence experiments, the expression of CD38 and HLA-DR was assessed on $CD34^+$ cells in eight samples of human fetal bone marrow. Four $CD34^+$ cell populations were identified: $CD38^-/HLA-DR^+$ (3%, SD 1); $CD38^+/HLA-DR^-$ (3%, SD 4); $CD38^-/HLA-DR^-$ (9%, SD 4); and $CD38^+/HLA-DR^+$ (85%, SD 6). See Table III.

TABLE III

Frequency of $CD34^+$ Cells in Fetal Bone Marrow and Frequency of Subpopulations as a Percentage of $CD34^+$ Cells

| Exp | $34^+$ | $38^-/DR^+$ | $38^+/DR^-$ | $38^-/DR^-$ | $38^+/DR^+$ |
|---|---|---|---|---|---|
| 1 | 6.4 | 3 | 5 | 11 | 81 |
| 2 | 16.2 | 2 | 2 | 5 | 91 |
| 3 | 8.1 | 5 | 9 | 12 | 74 |
| 4 | 26.4 | 4 | 3 | 4 | 89 |
| 5 | 14.8 | 3 | 2 | 4 | 91 |
| 6 | 15.4 | 3 | 3 | 5 | 89 |
| 7 | 14.9 | 2 | 1 | 15 | 82 |
| 8 | 7.4 | 3 | 2 | 13 | 84 |
| Mean |  | 3 | 3 | 9 | 85 |
| SD |  | 1 | 2 | 4 | 6 |

FIG. 2 illustrates a typical flow cytometric analysis of $CD34^+$ fetal bone marrow cells. The $CD38^-/HLA-DR^-$ cells were colored red; the $CD38^-/HLA-DR^+$ cells were colored yellow; the $CD38^+/HLA-DR^-$ cells were colored blue; and the $CD38^+/HLA-DR^+$ cells were colored gray. Phenotyping and cell sorting studies revealed that the $CD38^+$ cell populations were heterogeneous in morphology and expressed lineage associated antigens. The cell types within this population included myeloblasts, erythroblasts, lymphoblasts and megakaryoblasts. The $CD38^-/HLA-DR^+$ cells, on the other hand were homogeneous, primitive blast cells by morphology.

The four CD34+ cell fractions based on HLA-DR and CD38 expression (colored red, yellow, blue and gray in FIG. 2) were sorted singly into 96 well plates and assayed for their ability to form colonies in HSC Growth Medium. In eight experiments, average of 6% of the CD38−/HLA-DR− cells, 50% of the CD38−/HLA-DR+ cells, 35% of the CD38+/HLA-DR− cells and 16% of the CD38+/HLA-DR+ cells gave rise to hematopoietic colonies 14 days after cell sorting. In control experiments in which cells were sorted into the medium with 12.5% HS and 12.5% FCS, no colony formation was found. See Table IV (where plating efficiency is the number of single plated cells which generate colonies divided by the number of single plated cells multiplied by 100).

TABLE IV

Plating Efficiency of Single Cell Culture in CD34+ Subpopulations

| Exp | 38−/DR− | 38−/DR+ | 38+/DR− | 38+/DR+ |
|---|---|---|---|---|
| 1 | nd | 50 | nd | 35 |
| 2 | nd | 72 | nd | 13 |
| 3 | 19 | 45 | 44 | 19 |
| 4 | 5 | 21 | 24 | 14 |
| 5 | 10 | 62 | 24 | 14 |
| 6 | 4 | 67 | 33 | 9 |
| 7 | 5 | 76 | 38 | 10 |
| 8 | 0 | 35 | 39 | 9 |
| Mean | 6 | 50 | 35 | 16 |
| SD | 4 | 24 | 7 | 8 |

To assess the ability of these subpopulations to form colonies (i.e., to self-renew), the following procedures were used. Parts of the colonies formed as in Table IV were sacrificed for morphologic examination or to probe for cell surface antigen expression, whereas the remaining cells were dispersed and replated. The replated cells were cultures in identical media and were evaluated for colony formation after two weeks of culture. Only the CD34+/CD38−/HLA-DR− and CD34+/CD38−/HLA-DR+ populations gave rise to a substantial number of second generation hematopoietic colonies. See Table V (where replating efficiency is the number of replated wells which generated next generation colonies divided by the number of replated wells multiplied by 100. This is a measure of the ability of a cell to self-renew.) The second generation colonies were processed similar to the first generation colonies; however, only the cells originating from the single CD34+/CD38−/HLA-DR+ cells gave rise to third generation colonies and these gave rise to fourth generation colonies. A large expansion of cells was observed from the cells originating from the CD34+/CD38−/HLA-DR+ population. See Table V. Thus, the percentage of HSC as defined by this assay is at least 20%.

TABLE V

Replating Efficiency of CD34+ Subpopulations

| Gen | 38−/DR− | 38−/DR+ | 38+/DR− | 38+/DR+ |
|---|---|---|---|---|
| 1 | 6 | 50 | 37 | 14 |
| 2 | 50 | 72 | 6 | 0.8 |
| 3 | 0 | 49 | 0 | 0 |
| 4 | 0 | 14 | 0 | 0 |

The morphology of the sacrificed colonies from Table V showed that only in the colonies originating from the single CD34+/CD38−/HLA-DR+ cells were the majority of the cells primitive blasts. The percentage of blasts within the colonies decreased gradually in the second, third and fourth generations. See Table VI.

The ability of the CD34+/CD38−/HLA-DR+ populations to generate cells in each of the hematopoietic lineages is shown in Table VII. Single cells were plated in HSC Growth Medium. 116 single cells from first generation colonies then were replated. Neutrophils ("N"), monocytes/macrophages ("M"), osteoclasts ("O"), erythrocytes ("E"), eosinophils ("Eo"), lymphocytes ("L"), mast cells ("Mast") and megakaryocytes ("Meg") were found either after first, second or third replating of these cells. Some of the single cells in this phenotypic population gave rise to each of the hematopoietic lineages. See Table VII.

TABLE VI

Percentage of Blasts of Hematopoietic Colonies

| Gen | 38−/DR− | | | | | | 38+/DR+ | | | | | | 38+/DR− | | | | | | 38−/DR+ | | | | | |
|---|---|---|---|---|---|---|---|---|---|---|---|---|---|---|---|---|---|---|---|---|---|---|---|---|
| 1 | 4[a] | 0[b] | 0[c] | 0[d] | 25[e] | 75[f] | 2 | 0 | 0 | 50 | 50 | 0 | 22 | 9 | 9 | 18 | 5 | 59 | 42 | 36 | 12 | 14 | 14 | 24 |
| 2 | 0 | 0 | 0 | 0 | 0 | 0 | 0 | 0 | 0 | 0 | 0 | 0 | 8 | 0 | 0 | 13 | 25 | 63 | 23 | 30 | 22 | 12 | 12 | 22 |
| 3 | | | | | | | | | | | | | 0 | 0 | 0 | 0 | 0 | 0 | 7 | 0 | 0 | 14 | 29 | 57 |
| 4 | | | | | | | | | | | | | | | | | | | 6 | 0 | 0 | 0 | 0 | 100 |

[a] # of wells examined
[b] percentage of wells with ≧60% blasts
[c] percentage of wells with between 60% and 30% blasts
[d] percentage of wells with between 30% and 10% blasts
[e] percentage of wells with between 10% and 5% blasts
[f] percentage of wells with ≦5% blasts

TABLE VII

Frequencies and Predominance of Cell Lineages Originating from Single Sorted CD34+/CD38−/HIA-DR+ Cells

| | N | M | Ost | E | Eo | L | Mast | Meg |
|---|---|---|---|---|---|---|---|---|
| Freq | 90[a] | 95 | 8 | 39 | 9 | 15 | 22 | 15 |
| Pred | 42[b] | 44 | 0 | 9 | 0 | 2 | 3 | 0 |

[a] "90" is the percentage of the 116 wells in which neutrophils could be found in could be found in either the 2nd, 3rd or 4th generations upon replating
[b] "42" is the percentage of wells in which neutrophils were the predominant cells type Referring to FIG. 3, the majority of CD34+ cells co-express both CD38 and HLA-DR; however, three additional populations of cells can be identified: CD38+/HLA- DR⁻ cells wherein G₀/G₁/M phase cells were depicted in red and S/G₂ cells were depicted in violet; CD38⁻/HLA-DR⁺ cells wherein G₀/G₁ cells were depicted in blue and S/G₂/M cells were depicted in black; and CD38⁻/HLA-DR⁻ cells wherein G₀/G₁ cells were depicted in green and S/G₂/M cells were depicted in light blue. Cell cycle analysis of these cells revealed that 25% of CD38⁺/HLA-DR⁺ cells are in S, G₂ or M. Similarly, 19% of CD38⁺/HLA-DR⁻ and 15% of CD38⁻/HLA-DR⁻ were in S phase or G₂/M;; however, only 5% of the CD38⁻/HLA-DR⁺ cells were in S/G₂/M. See Table VIII. The majority of cells in this latter cell fraction, therefore, were resting in cell cycle which is a characteristic of HSC.

TABLE VIII

Analysis of Cell Cycle in CD34⁺ Subpopulations as a Percentage of G₂/M Cells in Cell Cycle

| Exp | 38⁺/DR⁺ | 38⁺/DR⁻ | 38⁻/DR⁻ | 38⁻/DR⁺ |
|---|---|---|---|---|
| 1 | 21 | 17 | 10 | 3 |
| 2 | 27 | 12 | 7 | 9 |
| 3 | 28 | 27 | 27 | 3 |
| Mean | 25 | 19 | 15 | 5 |
| SD | 3 | 6 | 9 | 3 |

For FIGS. 4–7, fetal bone marrows were obtained as set forth above. Erythrocytes were lysed as above and the cell suspensions washed. In order to investigate the possibility that antigens of low density were being expressed on cell populations enriched for HSC, a FACScan brand flow cytometer (BDIS) was modified so as to have three lasers illuminating the flow cell in the following sequence at intervals of 20μ seconds: 488 nm Argon laser to excite FITC and PerCP; 633 nm Helium Neon laser to excite APC; and a 532 nm YAG laser to excite PE. The latter laser excited PE so as to yield approximately 6 times higher signal to background (i.e., autofluorescence) ratio than results from excitation at 488 nm.

For these cell analysis experiments, cells were stained first with anti-CD33 PE, anti-CD13 PE or anti-CD71 PE at 0.1 μg per test for 20 minutes, and then the cells were washed. The cells then were stained simultaneously with anti-CD34 PerCP, anti-CD38 APC and anti-HLA-DR FITC at 0.1 μg per test for 20 minutes. The cells then were washed, and fixed in 0.5% paraformaldehyde.

Figure 4A:
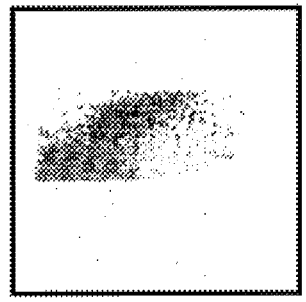
Figure 4B:
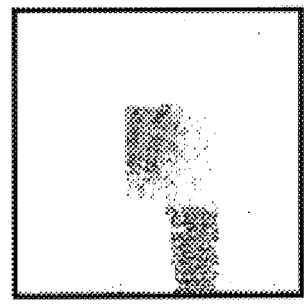
Figure 4C:
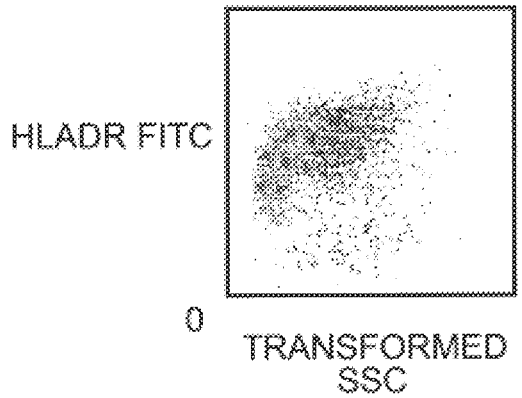
Figure 4D:
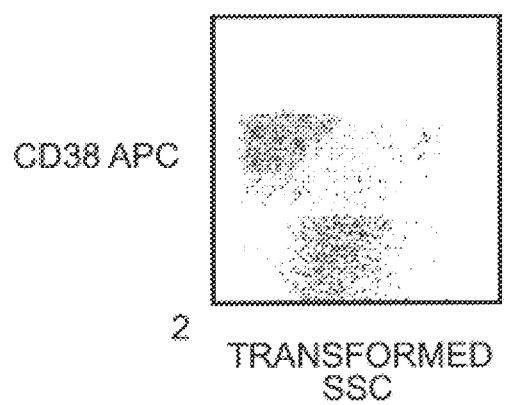
Figure 4E:
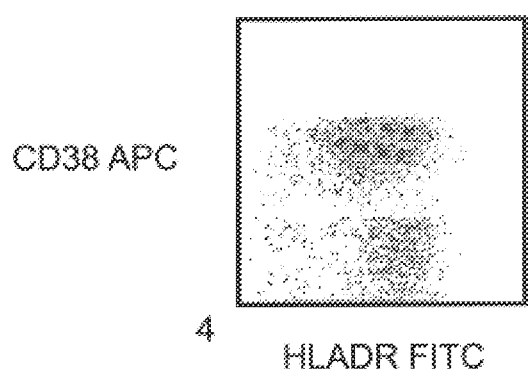
Figure 5A:
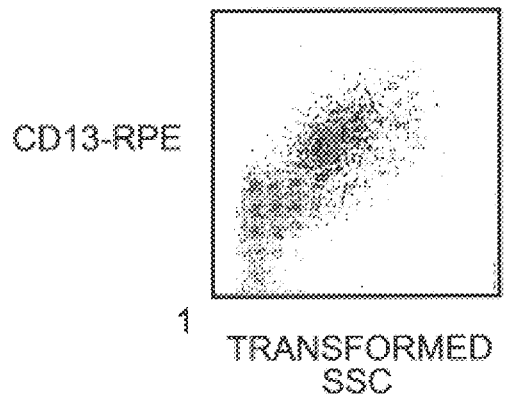
Figure 5B:
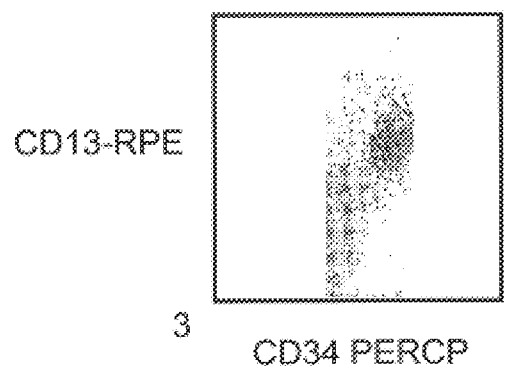
Figure 5C:
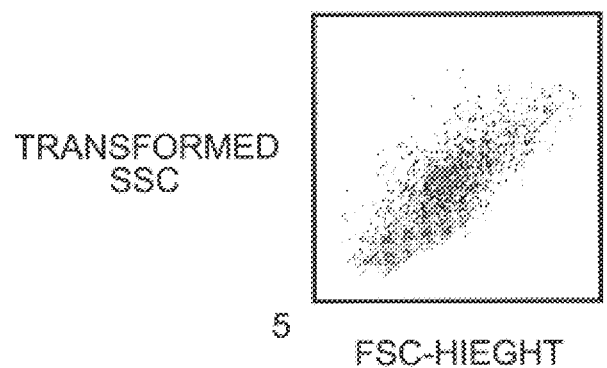
Figure 5D:
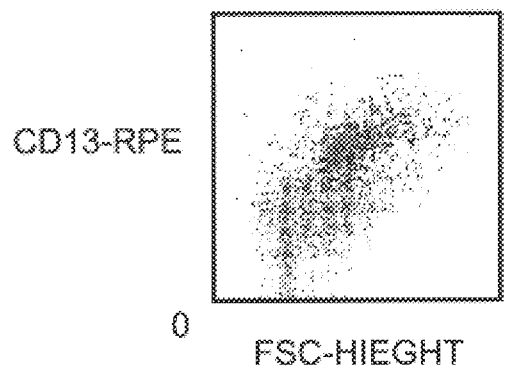
Figure 5E:
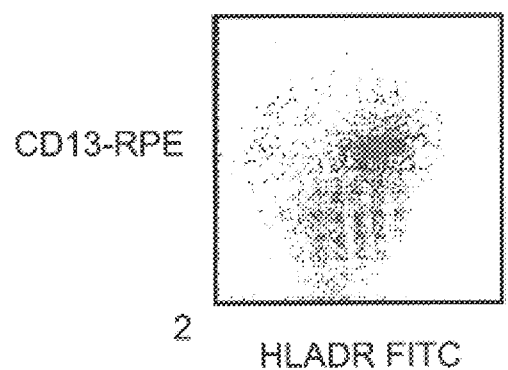
Figure 5F:
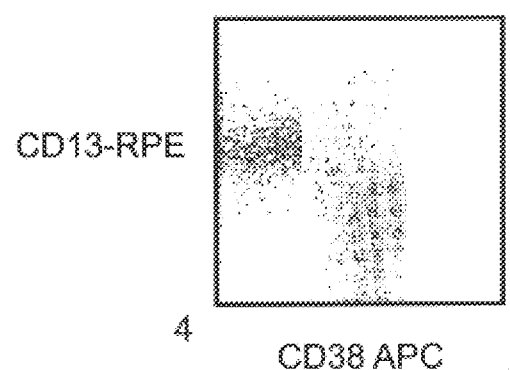
Figure 6A:
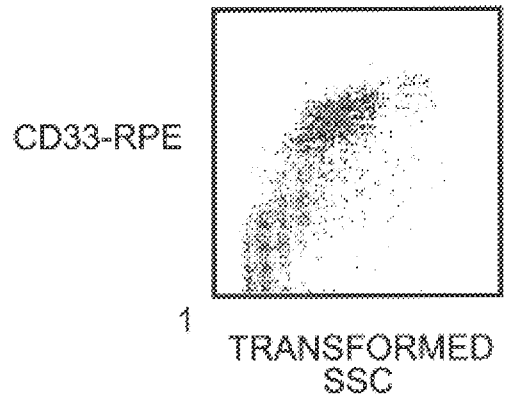
Figure 6B:
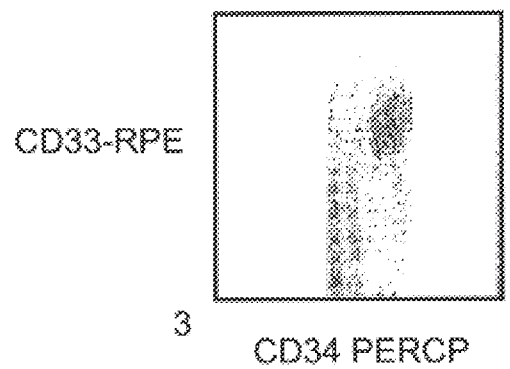
Figure 6C:
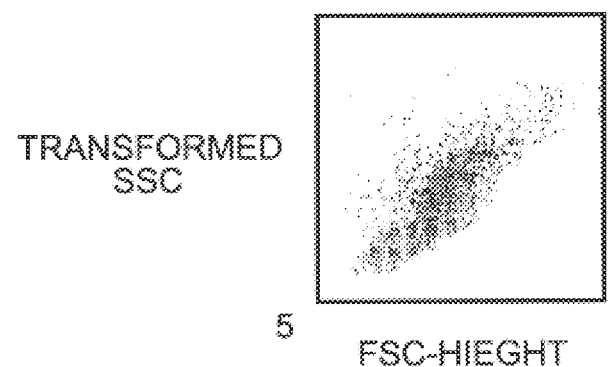
Figure 6D:
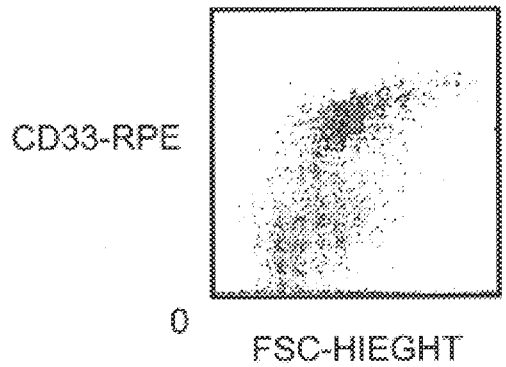
Figure 6E:
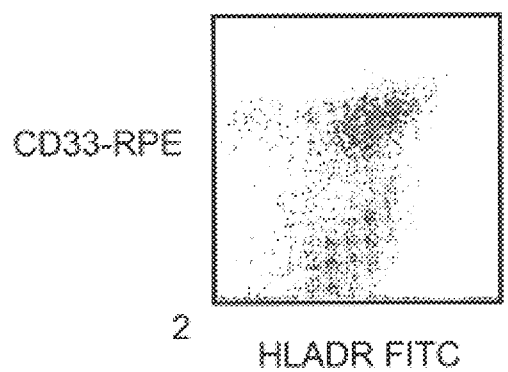
Figure 6F:
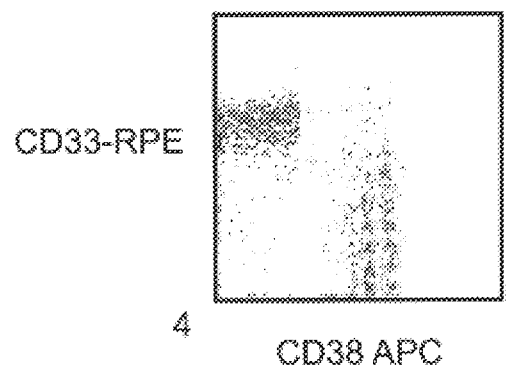
Figure 7A:
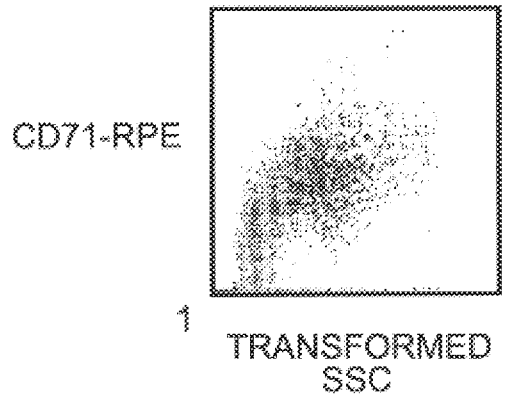
Figure 7B:
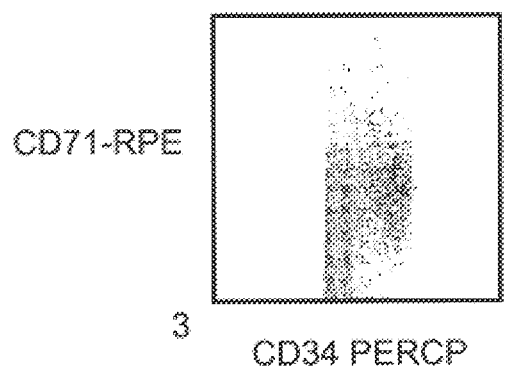
Figure 7C:
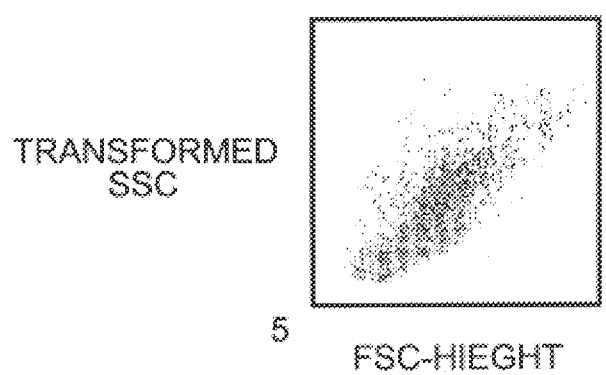
Figure 7D:
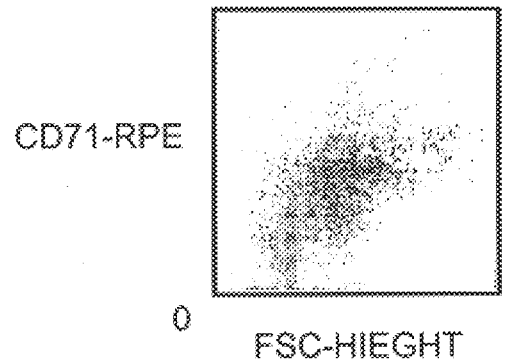
Figure 7E:
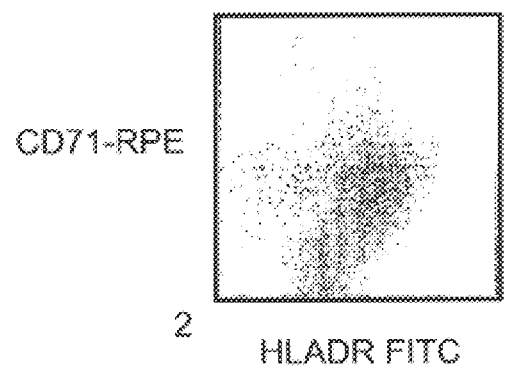
Figure 7F:
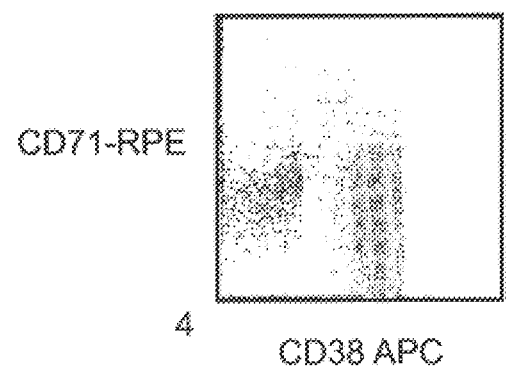

Referring to FIG. 4A, cells that are CD34⁺ are displayed in a plot of fluorescence versus transformed orthogonal light scatter. Myeloid cells (gray) have higher light scatter than lymphoid cells (yellow) while HSC are intermediate. In FIG. 4D, the cell population enriched for HSC is clearly distinguishable from myeloid and lymphoid committed cells based upon CD38 expression. See also FIG. 4B.

Referring to FIG. 5, CD13 is present on myeloid committed cells and the cell population enriched for HSC but not on lymphoid committed cells. Expression of CD13 on cells within the cell population enriched for HSC appears consistent. See FIG. 5F. CD13 is expressed in a similar manner on adult bone marrow.

Referring to FIG. 6, CD33 expression on all cell types appears similar to that for CD13. The same result holds for adult bone marrow expression.

Referring to FIG. 7, CD71 is expressed on myeloid committed cells. Expression of CD71 on HSC and lymphoid committed cells, however, appears mixed with most of the cells within the cell population enriched for HSC expressing "intermediate" amounts of CD71 while lymphoid committed cells express intermediate to negative amounts. See FIG. 7F. Adult bone marrow expression of CD71 does not appear to differ from fetal bone marrow expression.

In addition to CD13, CD33 and CD71, other markers believed to be lineage associate were tried. Among these were CD3, CD5, CD8, CD10, CD11b, CD14, CD15, CD16, CD19, CD20, CD22 and CD61. Using the same methods as set forth in FIGS. 4–7, none of these markers could be detected at the limits of sensitivity for this system on the cells within the cell population containing HSC.

In summary, HSC are found to be concentrated in a population of CD34⁺ cells that also are CD38⁻. HSC are even more concentrated in CD34⁺ cells that are both CD38⁻ and HLA-DR⁺. In addition, cell populations enriched for HSC now have been demonstrated to express CD13, CD33 and CD71 antigens in cells derived from both adult and fetal tissue.

Cell populations enriched for HSC can be selected by a variety of means, preferably flow cytometry. Cells from peripheral blood, cord blood, liver or spleen can be labelled with CD34 and CD38 monoclonal antibodies, and sorted based upon expression of CD34 and CD38. It is preferable to use HLA-DR in addition to CD34 and CD38. Other means for selecting cells are described in U.S. Pat. Nos. 5,215,927, 5,225,353, and 5,240,856; WO91/09141; and Kato et al., Cytometry, 14:384 (1993).

HSC, and populations of human cells lacking mature and progenitor lymphoid, myeloid and erythroid cells and enriched for HSC, have a number of therapeutic uses. Traditionally, bone marrow transplantation has been used to reconstitute a patient's marrow following ablative therapy. The down-side to such treatment has been and continues to be a graft-versus-host reaction ("GVHD") even in instances where HLA matching has been done. Civin, in U.S. Pat. No. 4,714,680, described the utility of transplanting CD34⁺ cells (i.e., stem and progenitor cells) as an alternative to whole marrow reconstitution in order to reduce the possibility of GVHD, and to increase the likelihood of engraftment.

The wide-spread use of CD34⁺ cells in transplantation, however, has not yet occurred. While there are a number of companies pursuing a variety of methods to harvest CD34⁺ cells for transplantation, the diseases to which these methods have been generally limited to those where conventional transplantation has been applied. One reason is the presence of residual tumor cells.

In grafts harvested for autologous bone marrow/peripheral blood transplantation from cancer patients, residual tumor can be found that can give rise to a relapse after transplantation. See Dill et al., Hum. Gene Ther., 3:129 (1992), and see Deisseroth et al., Blood, 82:1800 (Suppl. 1, 1993). Reduction of the tumor load or an increase in the purity of the infusate, therefore, is of major importance. Selection of CD34⁺ cells can reduce the number of residual tumor cells in an autograft. See Berenson et al., Blood, 82:678 (Suppl. 1, 1993). An increase in purity can be obtained by selection of the more primitive cells among the CD34⁺ cells by eliminating at least the CD38⁺ cells.

In addition to increasing the purity of the infusate, more aggressive chemo- and radiation therapies directed at the primary tumor can be pursued. Current treatments, for leukemias as well as epithelial cancers such as breast cancer, have not been entirely effective in attacking the primary tumor because of the destructive effects on marrow. By increasing the likelihood of complete engraftment, more aggressive approaches become possible.

Thus, by using CD34 in combination with CD38 and, preferably, HLA-DR, populations of cells enriched for HSC can be obtained that are enriched for HSC, thus promoting complete engraftment, and the number of tumor cells in autologous grafts can be reduced. These enriched populations of cells then can be either directly transplanted into the patient's peripheral blood or bone marrow or expanded ex vivo through the use of growth factors, such as SCF, IL-3 and IL-6, followed by transplantation.

The source for donor cells is preferably the patient. These cells can be obtained from the donor's bone marrow or from a donor's peripheral blood. In the latter instance, this can be proceeded by mobilization (or expansion) of the HSC therein by means of treating the donor with growth factors such as G-CSF or GM-CSF. Autologous donation greatly reduces the likelihood of inadvertent transmission of viral or other disease.

Beyond transplantation of HSC, gene therapy in hematopoietic cells has been considered as desirable. Gene therapy seeks to replace or substitute for cells within the hematopoietic system that produce defective proteins or enzymes. Such diseases include, β thalassemia, ADA deficiency, Gaucher's disease, PNA disease and others. In one example, the gene controlling adenosine deaminase production is defective. By replacing the cells of the hematopoietic system with proper functioning cells, the disease might be cured. HSC, preferably autologous, containing the normal gene provided a better vehicle than $CD34^+$ cells alone for the reasons set forth above.

To perform gene therapy, one needs to select, insert and then transplant the altered cell. Selection of HSC can be performed as described above. Insertion of the gene into the HSC can be accomplished by a number of means but preferably by means of retroviral mediated transfer. In this process, there are two key considerations: the titer of the viral vector and the cycling status of the HSC. The former is important because $CD34^+/CD38^-$ populations do not consist solely of HSC. They are enriched for HSC; therefore, successful transfer is more likely if the titer is high. A high titer viral vector can be made by selecting a retroviral construct that provides the genome for transmission and by selecting a packaging cell line that contain encapsidation-defective viral genomes. Such cell lines include Psi-CRE, Psi-CRIP, GP+E86 and others. Once having the proper vehicle, the gene can be isolated or created and inserted into the vector by means well known to those of ordinary skill. See, e.g., U.S. Pat. No. 5,032,407; Luskey et al., Blood, 80:396 (1992); Bregni et al., Blood, 80: 1418 (1992); Karlsson, Blood, 78:2481 (1991); Kwok et al., PNAS, 83:4552 (1986). It should be noted, however, that treatment of HSC with one or more of IL-3, SCF and IL-6 prior to transfection promotes gene transfer. See Bregni et al. Following this, transformed cells typically would be expanded ex vivo followed by transplantation into the patient. Further treatments with transformed HSC could be carried out at future dates is needed. See also Williams et al., Human Gene Therapy, 1:229 (1990); Nolta et al., Human Gene Therapy, 1:257 (1990); and Miller, Blood, 76:271 (1990).

Not all therapies, however, will involve replacement of defective genes. It is likely that in some instances, for example, sickle cell anemia, transplantation of HSC that will overexpress the normal β hemoglobin gene might be sufficient for therapeutic purposes.

All publications and patent applications mentioned in this specification are indicative of the level of ordinary skill in the art to which this invention pertains. All publication and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

We claim:

1. A population of human cells that lacks mature progenitor cells of the erythroid, lymphoid, and myeloid lineages and is enriched for hematopoietic stem cells wherein said stem cells are capable of limited self-renewal and differentiation into erythroid myeloid and lymphoid progenitors and mature cells, which population is comprised of cells having a $CD34^+/CD38^-/HLA\text{-}DR^+$ phenotype, wherein cells having said phenotype comprise at least 95% of said population.

2. The population of cells of claim 1 wherein said human cells are also at least one or more of $CD13^+$, $CD33^+$ and $CD71^+$.

3. The population of human cells of claim 1 wherein said cells are derived from fetal or adult tissue.

4. The population of human cells of claim 3 wherein said cells are derived from peripheral blood, cord blood, bone marrow, liver or spleen.

5. A population of human cells comprising hematopoietic stem cells wherein said human cells are of a phenotype $CD34^+/CD38^-/HLA\text{-}DR^+/CD13^+/CD33^+/CD71^+$, wherein cells of the phenotype comprise at least 95% of said population.

6. A method of isolating a population of human cells that lacks mature and progenitor cells of the erythroid, lymphoid and myeloid lineages and enriched for hematopoietic stem cells comprising the steps of obtaining human tissue containing hematopoietic stem cells, selecting said hematopoietic cells based upon the expression of at least CD34, HLA-DR, and CD38 antigens, and separating the cells that express CD34 and HLA-DR but do not express CD38, wherein said $CD34^+/HLA\text{-}DR^+/CD38^-$ cells comprise at least 95% of said population.

7. The method of claim 6 wherein the selection step is carried out with monoclonal antibodies.

8. The method of claim 7 wherein the monoclonal antibodies are fluorescently labelled and the selection and separation steps are carried out by means of flow cytometry.

9. The method of claim 6 wherein mature erythroid cells are removed as a preliminary selection step.

* * * * *